United States Patent
Geissler et al.

(10) Patent No.: US 8,492,580 B2
(45) Date of Patent: Jul. 23, 2013

(54) PROCESS FOR PREPARING ISOCYANATES

(75) Inventors: Bernhard Geissler, Kirchheim (DE); Eckhard Stroefer, Mannheim (DE); Andreas Schmidt, Schwarzheide (DE); Matthias Kloetzer, Kroppen (DE)

(73) Assignee: BASF SE, Ludwigshafen (DE)

( * ) Notice: Subject to any disclaimer, the term of this patent is extended or adjusted under 35 U.S.C. 154(b) by 275 days.

(21) Appl. No.: 13/125,895

(22) PCT Filed: Aug. 2, 2010

(86) PCT No.: PCT/EP2010/061177
§ 371 (c)(1),
(2), (4) Date: Apr. 25, 2011

(87) PCT Pub. No.: WO2011/015541
PCT Pub. Date: Feb. 10, 2011

(65) Prior Publication Data
US 2011/0207961 A1    Aug. 25, 2011

(30) Foreign Application Priority Data

Aug. 4, 2009  (EP) .................................. 09167199

(51) Int. Cl.
*C07C 263/00*  (2006.01)
(52) U.S. Cl.
USPC ........................................................ 560/345
(58) Field of Classification Search
None
See application file for complete search history.

(56) References Cited

U.S. PATENT DOCUMENTS

| | | | | |
|---|---|---|---|---|
| 5,220,069 A | * | 6/1993 | King et al. | 564/393 |
| 7,329,776 B2 | | 2/2008 | Kohlstruk et al. | |
| 2008/0249332 A1 | * | 10/2008 | Klotzer et al. | 560/344 |
| 2009/0275775 A1 | * | 11/2009 | Kloetzer et al. | 560/344 |
| 2010/0274046 A1 | * | 10/2010 | Kloetzer et al. | 560/336 |
| 2011/0021836 A1 | * | 1/2011 | Bock et al. | 564/305 |

FOREIGN PATENT DOCUMENTS

| | | |
|---|---|---|
| EP | 0 480 493 | 4/1992 |
| EP | 0 566 925 | 10/1993 |
| EP | 1 512 680 | 3/2005 |
| EP | 1 512 681 | 3/2005 |
| EP | 1 512 682 | 3/2005 |
| EP | 1 602 643 | 12/2005 |
| WO | 2007 036479 | 4/2007 |
| WO | 2008 025659 | 3/2008 |

OTHER PUBLICATIONS

International Search Report Issued Dec. 21, 2010 in PCT/EP10/061177 filed Aug. 2, 2010.
U.S. Appl. No. 13/058,026, filed Feb. 8, 2011, Franzke, et al.
U.S. Appl. No. 13/163,928, filed Jun. 20, 2011, Rosendahl, et al.
U.S. Appl. No. 13/964,647, filed Mar. 7, 2012, Mattke, et al.
U.S. Appl. No. 13/513,460, filed Jun. 1, 2012, Bock, et al.
U.S. Appl. No. 13/479,961, filed May 24, 2012, Stroefer, et al.
U.S. Appl. No. 13/008,457, filed Jan. 18, 2011, Bock, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to an improved multistage process for the continuous preparation of diisocyanates by reaction of the corresponding diamines with carbonic acid derivatives and alcohols to form low molecular weight monomeric urethanes and thermal dissociation of the latter.

20 Claims, No Drawings

PROCESS FOR PREPARING ISOCYANATES

The invention relates to an improved multistage process for the continuous preparation of diisocyanates by reaction of the corresponding diamines with carbonic acid derivatives and alcohols to form low molecular weight monomeric urethanes and thermal dissociation of the latter.

Industrial processes for preparing organic polyisocyanates, e.g. aromatic, aliphatic or cycloaliphatic polyisocyanates, are based on phosgenation of the corresponding organic polyamines to form polycarbamic acid chlorides and thermal dissociation of these to give the polyisocyanates and hydrogen chloride. Apart from the serious problems in respect of environmental protection, disposal and safety associated with the use of phosgene, these processes suffer from further critical disadvantages. Thus, the preparation of aliphatic or cycloaliphatic polyisocyanates gives only quite moderate space-time yields because of the relatively high basicity of the starting polyamines. A further disadvantage is the formation of undesirable by-products which, even when present in traces, can lead to severe discoloration of the polyisocyanates. In the case of the preparation of hexamethylene 1,6-diisocyanate (HDI), for example, a number of by-products and the most important of these, viz. 6-chlorohexyl isocyanate, has the additional disadvantage that it can be separated off from HDI only with a considerable outlay for distillation.

This type of process suffers from the problems of, in particular, the high conversion of chlorine via phosgene and carbamoyl chloride into hydrogen chloride, the toxicity of phosgene and the corrosive nature of the reaction mixture, the lability of the solvents which are generally used and the formation of halogen-comprising residues.

The thermal dissociation of (cyclo)aliphatic and in particular aromatic monourethanes and diurethanes into the corresponding isocyanates and alcohol has been known for a long time and can be carried out both in the gas phase at high temperatures and in the liquid phase at comparatively low temperatures.

The reaction of diamines with urea and alcohol results in formation of not only the desired dissociatable diurethanes but also, as by-products, carbonates and frequently also carbamic esters.

EP 566925 A2, EP 1512680 A, EP 1512681 A, EP 1512682 A and EP 1602643 A1 describe the preparation of diisocyanates by reaction of the corresponding diamines, urea and alcohol, optionally in the presence of carbonates and/or carbamic esters. These carbonates and carbamic esters are separated off from the reaction mixture by distillation and can optionally be recirculated to the reaction. A specific utilization or treatment of the carbonates which have been separated off apart from the purification by distillation does not occur. A further disadvantage is that simple recirculation of the carbonates to the reaction leads to accumulation in continuous operation. Since carbonates are strong alkylating agents, their presence in the reaction leads to alkylation of the diamine used, which after alkylation is therefore no longer available for isocyanate formation but instead remains as by-product in the reaction mixture.

These processes have the disadvantages that the carbonate formed in the reaction can be utilized only incompletely, if at all, by the simple recirculation to the reaction stage. Possible remaining uses of the carbonate which has been separated off are use as pure material outside the process or thermal utilization, i.e. combustion and utilization of the heat generated.

It is an object of the present invention to provide a process for preparing diisocyanates from diamines, urea and alcohol, in which the carbonate formed in the reaction can be used within the process.

This object has been able to be achieved by a process for preparing diisocyanates by reaction of the corresponding diamines with urea and at least one alcohol to form the corresponding urethane (urethanization) with formation of the carbonate of the alcohol used and dissociation of the urethane obtained in this way to give the isocyanate (urethane dissociation), in which at least part of the carbonate formed is separated off from the reaction mixture, reacted with ammonia outside the urethanization and the reaction mixture formed in this way is introduced into the urethanization.

The invention also provides a multistage process for the continuous preparation of diisocyanates by reaction of the corresponding diamine with urea and at least one alcohol to form the corresponding urethanes with formation of the carbonate of the alcohol used in at least one reactor and thermal dissociation of the urethanes, which comprises the following steps and in which a) diamine is mixed with urea in the presence of at least one chloride-free catalyst or preferably in the absence of catalysts and in the absence or preferably in the presence of at least one alcohol, b) the mixture obtained from a) is reacted in at least one residence reactor to form the corresponding urethane and carbonate, c) the ammonia formed is separated off, d) excess alcohol, carbonate and further low-boiling secondary components are separated off from the output from c), e) the urethane which has been freed of alcohol and low-boiling components from (d) is at least partly fed to a distillation, f) the urethanes in the distillate from (e) and any proportion of (d) which has not been fed to the distillation (e) are dissociated into the corresponding diisocyanate and alcohol in a continuous dissociation apparatus, g) the crude isocyanate obtained from (f) is purified in at least one distillation and distillation residues obtained are returned to the dissociation (f) and/or converted by means of alcohol into urethanes and fed to the reaction unit (b), h) the reaction output from (f), which comprises a high proportion of urethanes and utilizable compounds, is again converted into urethanes by reaction with at least one alcohol and this reaction mixture is fed to step a) and/or b) and i) the carbonate which has been separated off in d) is at least partly reacted with ammonia and the product of this reaction is fed to step a) and/or b).

The process of the invention gives more effective utilization of the carbonate formed as by-product than processes known from the prior art.

Purely formally, the process of the invention can be represented schematically by the following equation:

$$R-(NH_2)_n + nH_2N(CO)NH_2 + nR'OH \rightarrow R(NCO)_n + nR'OH + 2nNH_3$$

For the purposes of the present text, the term "carbonate" refers to the organic carbonate of the alcohol used, which has the formula $$R'-O-(CO)-O-R'.$$

The term "carbamic ester" refers to the ester of carbamic acid with the alcohol used, which has the formula $$R'-O-(CO)-NH_2.$$

Suitable amines for preparing the monomeric urethanes which can be used as intermediates are amines of the formula R(NH$_2$)$_n$, where R is a polyvalent, preferably divalent, organic radical, e.g. an optionally substituted aromatic radical, for example, an aromatic radical substituted by an alkyl group, or preferably a linear or branched, aliphatic or optionally substituted cycloaliphatic radical.

Examples of suitable aromatic polyamines are 2,4- and 2,6-toluenediamine, 4,4'-, 2,4'- and 2,2'-diaminodiphenylmethane and the corresponding isomer mixtures.

Possible aliphatic or cycloaliphatic polyamines are, for example: 1,4,-butanediamine, 2-ethyl-1,4-butanediamine, 1,8-octanediamine, 1,10-decanediamine, 1,12-dodecanediamine, 1,4-cyclohexanediamine, 2-methyl-, 4-methyl-1,3-cyclohexanediamine, 1,3- and 1,4-diaminomethylcyclohexane, 4,4'-di(aminocyclohexyl)methane and 3 (or 4), 8 (or 9)-bis(aminomethyl)tricyclo[5.2.1.0$^{2.6}$]decane isomer mixtures. Preference is given to using 2-methyl-1,5-pentanediamine, 2,2,4- or 2,4,4-trimethyl-1,6-hexanediamine, dicyclohexylmethylenediamine (H12MDA) and in particular 1,6-hexanediamine and 3-aminomethyl-3,5,5-trimethylcyclohexylamine.

Suitable alcohols are in principle all aliphatic and cycloaliphatic, preferably aliphatic alcohols. However, preference is given to selecting alcohols whose boiling points are sufficiently different from the boiling point of the diisocyanate obtained by thermal dissociation so that virtually quantitative separation of the dissociation products diisocyanate and alcohol is possible.

For these reasons, preference is given to using alcohols, such as methanol, ethanol, n-propanol, n-butanol, isobutanol, n-pentanol, isopentanol, n-hexanol, isohexanols, cyclopentanol, cyclohexanol, 2-ethylhexanol, decanol or mixtures of the alcohols mentioned, preferably methanol, n-butanol and/or isobutanol, but in particular n-butanol and/or isobutanol.

The individual steps of the process are described below:

a) Mixing of the Reaction Components

Mixing of the feed streams can be carried out in any apparatuses which are known per se to those skilled in the art. Mixing in step (a) can also be carried out jointly with the reaction in step (b). Mixing can preferably be carried out in a suitable separate mixing apparatus, particularly preferably in a special mixing apparatus which has short mixing times.

Separate mixing apparatuses are, for example, mixing circuits, stirred vessels, cascades of stirred vessels, tubes having static mixers or mixing pumps.

It is possible to separate or to combine step (a) (mixing) and (b) (urethane formation). Usually, depending on the reaction conditions, urethane formation will commence during mixing of the starting materials.

To produce urethanes in the reaction step (a), the diamine is reacted with urea and at least one, preferably precisely one, alcohol in a molar ratio of amine, urea and alcohol of 1:2-20:5-40 at temperatures of 50-300° C., in particular 180-220° C., under a pressure of from 0.1 to 30 bar, preferably 5-20 bar. Under these reaction conditions, average reaction times of from fractions of seconds to minutes are obtained for the process of the invention.

To prevent or reduce significant commencement of urethane formation during mixing of the components, it is generally sufficient to mix the components at a temperature below 150° C.

The reaction in reaction step (a) can be carried out in the presence of dialkyl carbonates, advantageously in an amount of from 0.1 to 30 mol %, preferably from 1 to 10 mol % or alkyl carbamates, advantageously in an amount of from 1 to 20 mol %, preferably from 5 to 15 mol %, based on diamine. In particular, mixtures of dialkyl carbonates and alkyl carbamates in the abovementioned mixing ratios originating from step i) according to the invention are used. As dialkyl carbonates and/or carbamic esters, preference is given to using those whose alkyl radicals correspond to the alkyl radical of the alcohol used.

As indicated above, the reaction in reaction step (a) can also be carried out in the presence of catalysts. These are advantageously used in amounts of from 0.001 to 20% by weight, preferably 0.001 to 5% by weight, in particular from 0.01 to 0.1% by weight, based on the weight of the amine.

Suitable catalysts are inorganic or organic compounds, which comprise one or more cations, preferably one cation, of metals of groups IA, IB, IIA, IIB, IIIB, IVA, IVB, VA, VB, VIB, VIIB, VIIIB of the Periodic Table of the Elements, as defined in Handbook of Chemistry and Physics 14th Edition, published by Chemical Rubber Publishing Co., 23 Superior Ave. N.E., Cleveland, Ohio.

Examples which may be mentioned are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt.

The catalyst can further comprise at least one anion, for example halides, such as chlorides and bromides, sulfates, phosphates, nitrates, borates, alkoxides, phenoxides, sulfonates, oxides, hydrated oxides, hydroxides, carboxylates, chelates, carbonates and thiocarbamates or dithiocarbamates.

If a catalyst is used, use is made according to the invention of a catalyst which does not have an increased corrosiveness, particularly preferably a catalyst which does not comprise chloride, very particularly preferably a catalyst which does not comprise halide. In particular, no catalyst is introduced into the reaction.

The catalysts can also be used in the form of their hydrates or ammoniates without significant disadvantages.

As typical catalysts, mention may be made by way of example of the following compounds: lithium methoxide, lithium ethoxide, lithium propoxide, lithium butoxide, sodium methoxide, potassium tert-butoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutoxide, aluminum trichloride, bismuth(III) chloride, copper(II) acetate, copper(II) sulfate, copper(II) nitrate, bis (triphenylphosphine oxide)copper(II) chloride, copper molybdate, silver acetate, gold acetate, zinc oxide, zinc chloride, zinc acetate, zinc acetylacetonate, zinc octoate, zinc oxalate, zinc hexylate, zinc benzoate, zinc undecylenate, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron (II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate and also mixtures thereof.

As preferred catalysts, mention may be made by way of example of the following compounds: lithium butoxide, aluminum acetylacetonate, zinc acetylacetonate, titanium tetrabutoxide and zirconium tetrabutoxide.

The mixing time in special mixing apparatuses having a short mixing time is usually from 0.0001 s to 2 s, preferably from 0.0005 to 1 s, particularly preferably from 0.001 to 0.5 s, very particularly preferably from 0.005 to 0.2 s and in particular from 0.007 to 0.1 s. For the present purposes, the mixing time is the time which elapses from the commencement of mixing until 97.5% of the fluid elements of the mixture obtained have a mixing fraction which, based on the value of the theoretical final value of the mixing fraction of the mixture obtained on reaching the state of perfect mixing, deviates by less than 2.5% from this final value of the mixing fraction (for the concept of the mixing fraction, see for example, J. Warnatz, U. Maas, R. W. Dibble: Verbrennung, Springer Verlag, Berlin Heidelberg New York, 1997, 2nd edition, p. 134.).

As mixing apparatus, preference is given to using a mixing circuit, a stirred vessel, a mixing pump or a nozzle mixing apparatus, for example, coaxial mixing nozzles, Y- or T-mixers or a vortex impinging jet mixing configuration, preferably a mixing circuit, a stirred vessel, a mixing pump or a nozzle mixing apparatus.

When using a mixing circuit or a stirred vessel as mixing apparatus it is important that the amine solution is injected at high velocity. The velocities are usually in the range from 10 to 100 m/s, preferably from 20 to 80 m/s.

Preference is given to using a mixing nozzle and a mixing pump as mixing apparatus. Particular preference is given to using a mixing nozzle as mixing apparatus. Here, it is important that both the alcohol feed stream and the amine feed stream are introduced into the mixing nozzle at high velocity. The velocities are in the range from 10 to 100 m/s, preferably from 20 to 80 m/s.

The pressure in the feed lines to the nozzle is considerably higher than in the outlet of the mixing nozzle, but usually not above 110 bar abs, preferably not above 100 bar abs; the pressure is particularly preferably from 5 to 95 bar abs, very particularly preferably from 10 to 50 bar abs and in particular from 10 to 30 bar abs.

The pressure at the outlet of the mixing apparatus is generally above the reaction pressure in step b), for example in the range from 5 to 100 bar, preferably from 10 to 80 bar, particularly preferably from 10 to 50 bar.

The temperature of the output from the mixing apparatus is generally in the range from 25 to 240° C., preferably 30-190° C. and particularly preferably 40-180° C.

Before the output from the mixing apparatus is introduced into step b), it can be brought to the temperature desired there by means of a heat exchanger. The transfer of the reaction output from step a) to the subsequent step can advantageously be effected via pressure regulating valves; the pressure at the outlet of step a) should be at least 1 bar above, preferably at least 2 bar above, particularly preferably at least 3 bar above, the pressure prevailing in step b).

b) Reaction of the Mixture from a)

The liquid phase leaving the mixing apparatus is then fed to at least one, preferably precisely one, reactor operated with two phases (gaseous/liquid). This can be an unbackmixed reactor, for example, a stirred vessel or preferably a reactor having little or no backmixing, for example, a tube reactor or cascade of stirred vessels. The mixture is preferably fed into a tube reactor or a plurality of reactors which approximate a tube reactor in terms of their residence time distribution as a result of the gas phase being conveyed in concurrent with the liquid phase.

The tube reactor should preferably be largely free of backmixing. This is achieved, for example, by the ratio of the diameter of the tube reactor to its length or by means of internals such as perforated plates, slotted plates or static mixers. The freedom from backmixing is preferably achieved by the ratio of length to diameter of the tube reactor.

Suitable tube reactors are, for example, tubes whose length to diameter ratio is greater than 5, preferably greater than 6, particularly preferably greater than 10.

The Bodenstein number of the tube reactor should be greater than 5, preferably greater than 6, particularly preferably greater than 10, very particularly preferably from 10 to 600 and in particular from 10 to 100.

One aspect which is important to the invention is the presence of a flow which is ideally plug flow and in reality approximates this to the required extent. For this purpose, axial mixing, i.e. mixing along the flow direction through the reactor, is reduced as far as possible and the flow is ideally turbulent.

This is, in practice, achieved by means of high flow velocities and low cross-sectional areas, for example, in flow tubes.

The tube reactor can have any orientation in space. It is preferably constructed as a vertical tube reactor through which the reaction mixture particularly preferably flows from the bottom upward.

The tube reactor can be isothermal or preferably temperature-controlled. Temperature control can be effected by heating through the outer wall or by means of internal tubes or plates. Heating is preferably effected through the outer wall.

Of course, the tube reactor can also comprise a plurality of tube sections connected in series, as long as freedom from backmixing is still ensured. If necessary, phase separators for separating liquid and gaseous phases can optionally be provided along the tube reactor, for example, between such tube sections, in which ammonia formed during the reaction can be separated off so that the equilibrium of the reaction is shifted.

To increase the production capacity, it is also possible according to the invention for a plurality of tube reactors to be connected in parallel.

If appropriate, further urea and/or alcohol or preferably amine can be introduced into the tube reactor, as indicated above, at one or more places, for example, at the beginning and in the middle of the tube reactor.

The average residence time in the tube reactor is generally from 10 seconds to 5 hours, preferably from 20 seconds to 20 minutes, particularly preferably from 30 seconds to 10 minutes.

To keep the gas throughput for the next stage low, the output from the tube reactor can, in a preferred embodiment, be fed to a phase separator and the liquid phase taken off from the phase separator can then be fed to the next stage.

Such a phase separator is a vessel in which phase separation of gas and liquid phases is achieved by calming of the two-phase flow exiting from the concurrent reactor.

The phase separator can be isothermal or preferably heated in order to prevent precipitation of sparingly soluble by-products. Heating can, for example, be effected via the outer wall or by means of a circuit comprising an external heat exchanger. When an external heat exchanger is used, normal insulation of the heat exchanger is sufficient.

The temperature in the tube reactor and in any phase separator present is generally in the range from 50° C. and 300° C., preferably from 180° C. to 220° C.

The pressure in step b) is generally in the range from 0.1 bar abs to 30 bar abs and preferably from 5 to 20 bar abs.

The transfer of the reaction output from step b) into the next step can advantageously be effected via pressure regulating valves; the pressure in step b) should generally be at least 0.1 bar above the pressure prevailing in step c). If this is not the case, the transfer can be effected, for example, by means of a pump or barometrically.

The residence time in step b) is selected so that the conversion, based on amino groups in the diamine used into urethane groups, after leaving the (tube) reactor is at least 95%, preferably at least 98%, particularly preferably at least 99%, very particularly preferably at least 99.5% and especially at least 99.8%. Reaction conditions which lead to complete conversion are desirable.

The total residence time in steps a) and b) together is usually less than 10 hours, preferably less than 6 hours and particularly preferably less than 4 hours.

The reaction mixture leaving (b) can, if the amine groups have been converted completely into the urethane, be fed directly to the ammonia removal (c) or it is fed to a further reactor or reactor system in order to achieve complete conversion. Reactors which can be used are further tube reactors, cascades of mixing reactors or columns having the necessary average residence time.

If the conversion, based on amino groups in the diamine used into urethane groups, after leaving the tube reactor is not yet complete and is, for example, less than 95%, the output can be subjected to an after-reaction.

For this purpose, the reaction can be allowed to undergo an after-reaction in a further tube reactor or else in a backmixed reactor in order to complete the conversion, preferably until the conversion is 98% or more.

For the present purposes, a backmixed reactor system is one in which the Bodenstein number of the reactor system is less than 5, preferably less than 4.

c) Ammonia Removal

To separate off the ammonia, it is advantageous to use columns, and the ammonia is preferably separated off by distillation. This gives good separation between the alcohol and ammonia. The removal is usually carried out in a pressure range of 0.01-20 bar, preferably 0.04-15 bar. The temperatures necessary depend on the alcohol or alcohol mixture used. In the case of n-butanol, the temperature is, for example, 60-150° C., preferably from 80 to 140° C.

It has been found to be advantageous for the ammonia formed to be removed immediately from the reaction mixture so that deposits of ammonium carbamate, which is formed in small amounts from ammonia and carbon dioxide by decomposition of urea, can be avoided.

This distillation unit is of a type known per se and has the usual internals. Possible column internals are in principle all customary internals, for example, trays, ordered packing and/or random packing. Among trays, preference is given to bubble cap trays, sieve trays, valve trays, Thormann trays and/or dual-flow trays, and among random packing, preference is given to packing with rings, helices, saddle bodies, Raschig Intos or Pall rings, barrel or Intalox saddles, Top-Pak etc. or braids. Preference is given to using ordered packing.

The distillation column preferably has 10-20 theoretical plates.

d) Removal of the Excess Alcohol

The ammonia-depleted reaction mixture obtained is then subjected to removal of alcohol, the dialkyl carbonate comprised or alkyl carbamate present in the reaction mixture, should this have been formed, or mixtures of at least two of these components and is fed at least partly to step i) according to the present invention.

To separate off the components, the reaction mixture is advantageously depressurized from the pressure level of reaction step (b) to a pressure in the range from 1 to 500 mbar, preferably from 2 to 100 mbar. This gives gaseous vapors which comprise predominantly alcohol and also from 1 to 30% by weight, preferably from 2 to 10% by weight of dialkyl carbonate and/or from 1 to 50% by weight, preferably from 5 to 15% by weight, of alkyl carbamate and a liquid output which consists essentially of the monomeric diurethane and may comprise oligourea polyurethanes and high-boiling oligomers.

The vapors obtained ($d_L$) are separated in subsequent purification steps, advantageously by distillation, preferably by rectification, and the products of value alcohol, carbonate and alkyl carbamate isolated here are recirculated individually or as a mixture, preferably to reaction step (a) for formation of the monomeric urethanes, or at least partly fed to step (i) according to the invention.

In a preferred embodiment of the present invention, at least part of the carbonate-comprising vapors ($d_L$) which have been separated off is fed to step (i) according to the present invention. Furthermore, another part of the carbonate-comprising vapors ($d_L$) which have been separated off can be fed to step (a).

The ratio of the stream fed to step (a) to the stream fed to step (i) is from 0:100 to 90:10, preferably from 10:90 to 90:10, particularly preferably from 20:80 to 80:20.

As an alternative to this separation just described, it is also possible to separate off essentially only the alcohol as low boiler from the reaction mixture in a first distillative separation and to subject the distillation bottoms, which comprise diurethane together with dialkyl carbonate and optionally alkyl carbamate, to a further distillation in which dialkyl carbonate and optionally alkyl carbamate are separated off as low boilers and the diurethane remains in the distillation bottoms and is passed to the next step. Carbonate and carbamic ester are then, as described above, introduced at least partly into step i) and any remaining part which has not been introduced into step i) is fed to step a) and/or b).

A flash evaporator is frequently used for the removal of the alcohol or the alcohol mixture by distillation. This apparatus can be a vessel or a combination of vessel and column, preferably a column, from which the alcohol or the alcohol mixture can be taken off at the top and the urethane can be taken off at the bottom. The product from the top of the column can comprise not only the alcohol but also further materials which have boiling points lower than that of the urethane. The separation is carried out in a pressure range from 0.001 to 2 bar, preferably 0.02-0.5 bar.

e) Urethane Purification

The liquid reaction mixture (d) comprising the monomeric diurethanes and possibly oligourea polyurethanes and high-boiling oligomers which is generally obtained as a bottom product in reaction step (d) after the vapors have been separated off can either all be fed to the next stage or is preferably divided into two substreams in a weight ratio of 5-50:95-50, preferably 10-30:90-70.

The equal-sized or preferably larger substream is separated off by distillation in a customary distillation unit, preferably a thin film evaporator, at a temperature of from 170 to 240° C., preferably from 180 to 230° C., under a pressure of 0.001-1 bar, preferably 0.002-0.01 bar, into a product of value which comprises the diurethanes and the relatively low-boiling by-products ($e_L$) and by-products ($e_H$), which cannot be distilled and are separated off from the production process and usually discarded as unusable residue. The product of value (distillate) is combined with the equal-sized or preferably larger other substream and the combined diurethane-comprising reaction mixture is fed to the thermal dissociation (f).

As a result of this process measure in reaction step (e) the proportion of undistillable by-products in the reaction mixture which are formed during the successive part reactions and would continually increase in concentration in the reaction circuit as a result of the recirculation of usable starting material, is limited to a content of from 3 to 30% by weight, preferably from 5 to 20% by weight and a reaction which proceeds without problems in high selectivity is thereby ensured.

As distillation apparatuses it is possible to use thin film evaporators or short path evaporators. The urethane is distilled at pressures of 0.001-1 bar, preferably in the range 0.002-0.01 bar. The distillate ($e_L$) is fed to the dissociation (f).

The high-boiling bottoms ($e_H$) are preferably discarded or can, less preferably, be partly fed to the reurethanization (h).

In a preferred embodiment, any residual content of monomers is separated off from these bottoms comprising high boilers. This can be effected, for example, as described in the international patent application WO 2007/036479 which is hereby incorporated by reference into the present disclosure.

The bottoms comprising high boilers are preferably treated at a temperature in the range from 210 to 330° C. and a pressure below 300 hPa so that the usable constituents, for example monomers, are driven off. This treatment preferably takes place in one of the following apparatuses:
a) paddle driers, preferably without a cooling zone, preferably with positive discharge devices,
b) vented extruders and
c) vertical thin film processors having positive discharge devices.

Particular preference is given to a paddle drier.

f) Urethane Dissociation

The diurethane comprising reaction mixture obtained in reaction step (e) is thermally dissociated continuously in a suitable apparatus, preferably in the absence of solvent in the liquid phase in the presence of catalysts at temperatures of from 200 to 300° C., preferably from 220 to 280° C., under a reduced pressure of 0.01-0.6 bar, preferably in the range 0.02-0.1 bar. The conversion of the urethane in the thermal dissociation apparatus can be selected largely freely as a function of the urethane used and is advantageously in the range from 10 to 98% by weight, preferably from 40 to 90% by weight, of the amount of urethane fed in.

The undissociated part of the reaction mixture, which comprises unreacted urethanes, oligourea polyurethanes, high-boiling oligomers and other reusable and unusable by-products, is separated off, discharged continuously ($f_H$) from the dissociation apparatus and recirculated directly or, if appropriate, after reaction with alcohol in the reurethanization (h) to reaction step (a) and/or (b).

Catalysts used for the chemical dissociation of urethanes are, for example, the abovementioned inorganic and organic compounds which catalyze urethane formation.

Catalysts which have been found to be particularly useful and are therefore preferably used are dibutyltin dilaurate, iron(III) acetylacetonate, cobalt(II) acetylacetonate, zinc acetylacetonate, zirconium tetra-n-butoxide and tin(II) dioctoate. Suitable dissociation apparatus are, for example, cylindrical dissociation reactors such as tube furnaces or preferably evaporators, for example thin film evaporators or bulk evaporators, e.g. Robert evaporators, Herbert evaporators, Caddie-type evaporators, plate crackers, glow plug evaporators, preferably plate crackers.

The separation of the dissociation products is effected in a column in which the isocyanate is usually taken off at the side ($f_M$) and the alcohol ($f_L$) is usually taken off at the top.

In a preferred embodiment, the overhead fraction obtained in the purification of the crude isocyanate (f) by distillation is recirculated to reaction step (a), the side fraction, which consists essentially of pure isocyanate, is taken to a container for storage and the bottom fraction is returned to reaction step (a) or (d) or (a) and (d).

g) Isocyanate Purification

The crude isocyanate mixture is freed of recombination products, by-products and, if present, the solvent in a subsequent distillation. The by-products are preferably recirculated to the thermal dissociation. A part thereof can also be discharged.

The dissociation products formed in the thermal dissociation, which are composed predominantly of alcohol, diisocyanate, and partially dissociated urethanes, are then advantageously separated with the aid of one or more distillation columns, preferably by rectification at temperatures of from 100 to 240° C., preferably from 120 to 200° C. and a pressure of from 1 to 200 mbar, preferably from 5 to 50 mbar, into low boilers and in particular alcohol ($g_L$) and a crude isocyanate mixture ($g_M$) having an isocyanate content of from 85 to 99% by weight, preferably from 95 to 99% by weight. The relatively high-boiling by-products ($g_H$) and in particular the undissociated and partially dissociated urethanes obtained in the separation by distillation are preferably fed to the dissociation apparatus (f) and/or reurethanization (h).

The index "L" here denotes low-boiling streams in the individual steps, the index "H" denotes high-boiling streams and "M" denotes middle-boiling streams.

The crude isocyanate mixture ($g_M$) which is preferably obtained by rectification is purified by distillation at a temperature of from 100 to 180° C. and a pressure of from 1 to 50 mbar, with the individual fractions being recirculated or isolated as pure product. As indicated above, the overhead fraction obtained in the pure distillation which is preferably employed, which preferably comprises diisocyanate, is, if appropriate after reaction of the free isocyanate groups with alcohol, recirculated to reaction step (a) and/or (b), the side fraction, which comprises pure diisocyanate, preferably having a purity of at least 98% by weight, in particular above 99.8% by weight, is conveyed away to storage and the bottom fraction, which comprises the partially dissociated urethanes and isocyanates as significant components, is preferably recirculated to the dissociation apparatus for thermal dissociation.

However, in other process variants, the bottom fraction ($g_H$) can also be recirculated to the distillation column (d) for separation of the crude diisocyanate and alcohol or to reaction step (a) and/or (b), viz. urethane formation. It is also possible for the bottom fraction to be divided into 2 or 3 product streams, which are preferably recirculated to urethane formation (a) and/or the dissociation apparatus (f) and, if appropriate, to the distillation column (g) and/or the reurethanization (h).

h) Reurethanization

The reaction of the reaction output ($f_H$) from f) and/or distillation residues ($g_H$) from (g) are preferably fed back to the process. Here, the isocyanate groups and/or allophanates and/or ureas or other reactive constituents are reacted with alcohol and converted to urethanes. It is possible to carry out these reactions in separate reactors such as mixing reactors or flow tubes or else in (b). The alcoholysis of the residues requires temperatures of 100-250° C., preferably 150-220° C. The average residence times here are in the range from a few minutes to hours. In general, the reaction is preferably carried out in a single liquid phase. The pressure during the reaction does not play any particular role apart from the fact that it should be sufficient to keep the reaction mixture in the liquid phase.

For this purpose, the streams ($f_H$) and/or ($g_H$) and, if appropriate, part of the stream ($e_H$) for example, can be combined with alcohol in such amounts that the molar ratio of NCO groups or equivalents thereof, i.e. for example, urethane groups, to hydroxy groups is up to 1:100, preferably up to 1:20, particularly preferably up to 1:10.

The alcohol can, for example, be the low-boiling stream ($d_L$) from step (d) and/or the alcohol-comprising stream ($f_L$) from the urethane dissociation (f) and/or fresh alcohol.

The reaction mixture is reacted in the presence of or absence of catalysts for a period of from 1 to 150 min, preferably from 3 to 60 min at a temperature of from 20 to 200° C., preferably from 50 to 170° C., and a pressure of from 0.5 to 20 bar, preferably from 1 to 15 bar.

If a catalyst is to be used, it is preferably the same catalyst as in the urethane formation step (b).

The reaction can be carried out in a continuous cascade of vessels or in a tube reactor. Possible catalysts are in principle all compounds which promote the reaction of NCO groups with OH groups. Examples which may be mentioned are tin octoate, dibutyltin dilaurate, tin chloride, zinc dichloride, tin(II) dioctoate and triethylamine.

i) Reaction of the Carbonate

According to the invention, at least one carbonate-comprising stream is reacted with ammonia to convert at least part of the carbonate into the corresponding carbamic ester.

The carbonate-comprising stream can comprise carbonate together with alcohol in amounts of up to 5% by weight and carbamic esters in amounts of up to 25% by weight. In addition, ammonia can be comprised in amounts of up to about 0.5% by weight. Further components can be comprised in likewise small amounts if they have a volatility in the range between the boiling points of carbamate and carbamic ester.

In step (i), ammonia is reacted with carbonate in a molar ratio of from 1:1 to 100:1, preferably 1.5:1 to 80:1 and particularly preferably 2:1 to 50:1.

The temperature in the reaction should generally be from 50 to 250° C., preferably from 50 to 200° C. and particularly preferably from 60 to 180° C.

The reaction time is generally from 1 minute to 6 hours, preferably 5 minutes to 4 hours and particularly preferably from 10 minutes to 2 hours.

The pressure in the reaction should be from 1 bar (abs) to 50 bar, preferably from 2 to 40 bar, particularly preferably from 3 to 30 bar and very particularly preferably from 5 to 20 bar.

At least one catalyst as described under (a) can optionally be present in the reaction; preference is given to at least one catalyst being present.

Step (i) can be carried out batchwise or continuously, preferably continuously.

The reaction is preferably carried out with continual removal of the alcohol formed, for example in a cascade of stirred vessels with superposed distillation columns or in a reaction distillation.

Step (i) particularly preferably takes place in a tube reactor, with the reaction mixture being depressurized at the end in order to separate off the ammonia:

In a further embodiment, the carbonate obtained from step d) is separated from the other low and middle boilers by distillation, vaporized in an evaporator at temperatures of 100-250° C. and reacted with ammonia gas in the gas phase in a tube reactor. The pressure in this residence reactor can be set to 20 mbar-10 bar, preferably from 10 mbar to 9 bar, particularly preferably from 1 to 8 bar, very particularly preferably from 1.1 to 7 bar and in particular from 1.2 to 6 bar abs. In an embodiment of the gas-phase reactor, the reaction is accelerated at a catalytically active surface.

If the gas-phase reaction is carried out at elevated pressure, a preferred embodiment comprises depressurizing the reaction mixture to atmospheric pressure and condensing the liquid reaction products. The excess ammonia can subsequently be compressed and recirculated to the reaction or utilized thermally, for example as described in WO 2008/025659.

This can be effected in a separate separation, but also, for example, in the above-described step c).

The reaction mixture from step (i), in which at least part of the carbonate has been converted into carbamic ester, can then be fed to step a) and/or b).

However, the reaction mixture from step (i) is, particularly preferably after removal of the ammonia as described, preferably fed to step (d) and separated there by distillation into a predominantly carbonate-comprising stream and a stream comprising predominantly carbamic ester. The carbonate-comprising stream is from there fed back to step i) and the stream comprising carbamic ester is introduced into step a) and/or b).

The multistage process of the invention for the continuous preparation of diisocyanate with recirculation and discharge of the by-products enables the carbonate formed as by-product to be utilized effectively.

The diisocyanate prepared in this way is highly suitable for the production of polymers comprising urethane, isocyanurate, amide and/or urea groups by the polyisocyanate polyaddition process. They are also used for preparing polyisocyanate mixtures modified with urethane, biuret and/or isocyanurate groups. Such polyisocyanate mixtures derived from aliphatic or cycloaliphatic diisocyanates are used, in particular for producing light-stable polyurethane paints and coatings.

The following examples illustrate the invention but do not restrict it to these examples.

EXAMPLES

Example 1

Reaction in the Liquid Phase 600 g of a mixture of 77% of di-n-butyl carbonate, 11% of O-butyl carbamate, 2% of n-butanol and further secondary compounds are placed in a 1.5 liter reactor provided with a stirrer. In addition, 500 ppm of catalyst are added to the mixture. Zirconium tetrabutoxide was used as catalyst. The pressure of 5 bar is kept constant during the subsequent reaction with an attached ammonia bottle. The reactor is quickly heated up to 210° C. and is stirred for four hours. It is then cooled and depressurized. The reaction mixture comprises 24.6% of di-n-butyl carbonate, 38% of O-butyl carbamate and 26.2% of n-butanol. The carbonate conversion was about 68%.

Comparative Example 1

In a comparative example analogous to example 1, the reaction was carried out using nitrogen instead of ammonia. No conversion could be observed.

Example 2

Gas-Phase Reaction

In a converted gas chromatograph coupled to a mass spectrometer and having a column having a diameter of 0.1 mm and a length of 4 meters, a conversion of 52.8% of the injected di-n-butyl carbonate could be detected at an injector, oven and detector temperature of 200° C. A mixture of 50% of ammonia with helium was used as carrier or reaction gas. Analysis was effected via the characteristic fragments of the compounds. Calibration with a tracer was necessary.

The invention claimed is:

1. A process for preparing at least one diisocyanate, comprising:
    (A) reacting at least one of at least one corresponding diamine with urea and at least one alcohol to form a corresponding urethane and a corresponding carbonate of the at least one alcohol, in a first reaction mixture; and
    (B) dissociating the corresponding urethane obtained to give the isocyanate;
    (C) separating off at least part of the corresponding carbonate formed from the first reaction mixture, to obtain a separated carbonate;
    (D) reacting the separated carbonate with ammonia outside the reacting (A), to give a second reaction mixture; and
    (E) introducing the second reaction mixture into the reacting (A).

2. The process of claim 1, wherein the first reaction mixture from the reacting (A) is substantially freed of ammonia to give a resulting mixture, and
    alcohol, carbonate and, if present carbamic ester are separated off from the resulting mixture to give the separated carbonate, and
    the separated carbonate is at least partly reacted with ammonia.

3. The process of claim 2, wherein reacting ammonia with the separated carbonate is carried out at a molar ratio of from 1:1 to 100:1.

4. The process of claim 1, wherein the reacting (D) of ammonia with the separated carbonate is carried out at from 50 to 250° C.

5. The process of claim 1, wherein the reacting (D) of ammonia with the separated carbonate is carried out in the presence of at least one catalyst.

6. The process of claim 1, wherein the reacting (D) of ammonia with the separated carbonate is carried out with continual removal of an alcohol formed.

7. The process of claim 1, wherein the at least one diamine is selected from the group consisting of dicyclohexylmethylenediamine (H12MDA), 1,6-hexanediamine, and 3-aminomethyl-3,5,5-trimethylcyclohexylamine.

8. The process of claim 1, wherein the at least one alcohol is selected from the group consisting of methanol, n-butanol, and isobutanol.

9. The process of claim 1, wherein the reacting (D) of ammonia with the separated carbonate is carried out at a molar ratio of from 1:1 to 100:1.

10. The process of claim 9, wherein the reacting (D) of ammonia with the separated carbonate is carried out at from 50 to 250° C.

11. The process of claim 3, wherein the reacting (D) of ammonia with the separated carbonate is carried out in the presence of at least one catalyst.

12. The process of claim 4, wherein the reacting (D) of ammonia with the separated carbonate is carried out in the presence of at least one catalyst.

13. The process of claim 9, wherein the reacting (D) of ammonia with the separated carbonate is carried out in the presence of at least one catalyst.

14. The process of claim 3, wherein the reacting (D) of ammonia with the separated carbonate is carried out with continual removal of an alcohol formed.

15. The process of claim 4, wherein the reacting (D) of ammonia with the separated carbonate is carried out with continual removal of an alcohol formed.

16. The process of claim 9, wherein the reacting (D) of ammonia with the separated carbonate is carried out with continual removal of an alcohol formed.

17. The process of claim 9, wherein the at least one diamine is selected from the group consisting of dicyclohexylmethylenediamine (H12MDA), 1,6-hexanediamine, and 3-aminomethyl-3,5,5-trimethylcyclohexylamine.

18. The process of claim 3, wherein the at least one diamine is selected from the group consisting of dicyclohexylmethylenediamine (H12MDA), 1,6-hexanediamine, and 3-aminomethyl-3,5,5-trimethylcyclohexylamine.

19. The process of claim 7, wherein the at least one alcohol is selected from the group consisting of methanol, n-butanol, and isobutanol.

20. The process of claim 9, wherein the at least one alcohol is selected from the group consisting of methanol, n-butanol, and isobutanol.

* * * * *